(12) United States Patent
Muguruma et al.

(10) Patent No.: US 8,932,867 B2
(45) Date of Patent: Jan. 13, 2015

(54) HIGH PURITY HEPARIN AND PRODUCTION METHOD THEREFOR

(75) Inventors: Michio Muguruma, Miyazaki (JP); Hiroshi Murata, Osaka (JP)

(73) Assignees: University of Miyazaki, Miyazaki (JP); Fuso Pharmaceutical Industries Ltd., Osaka (JP)

( * ) Notice: Subject to any disclaimer, the term of this patent is extended or adjusted under 35 U.S.C. 154(b) by 0 days.

(21) Appl. No.: 13/822,825

(22) PCT Filed: Sep. 13, 2011

(86) PCT No.: PCT/JP2011/070851
§ 371 (c)(1),
(2), (4) Date: Mar. 13, 2013

(87) PCT Pub. No.: WO2012/036152
PCT Pub. Date: Mar. 22, 2012

(65) Prior Publication Data
US 2013/0183764 A1 Jul. 18, 2013

(30) Foreign Application Priority Data
Sep. 14, 2010 (JP) .................................. 2010-205310

(51) Int. Cl.
*C08B 37/00* (2006.01)
*A61K 31/727* (2006.01)
*G01N 30/14* (2006.01)

(52) U.S. Cl.
CPC ............ *C08B 37/0075* (2013.01); *A61K 31/727* (2013.01); *C08B 37/0003* (2013.01); *G01N 30/14* (2013.01); *C08B 37/0078* (2013.01)
USPC .................................. 436/94; 436/93; 436/91

(58) Field of Classification Search
CPC .. C08B 37/00; C08B 37/006; C08B 37/0063; C08B 37/0075
USPC ............................................... 436/94, 93, 91
See application file for complete search history.

(56) References Cited

U.S. PATENT DOCUMENTS

2002/0169143 A1* 11/2002 Sasisekharan et al. .......... 514/54
2007/0161073 A1* 7/2007 Sasisekharan et al. .......... 435/18

FOREIGN PATENT DOCUMENTS

JP      2002-293804      9/2002
WO      02/23190 A2      3/2002

OTHER PUBLICATIONS

Bultel L. et al, UV-MALDI-TOF Mass Spectrometry Analysis of Heparin Oligosaccharides Obtained yb Nitrous Acid Controlled Degredation and High Performance Anion Exchange Chromatography,Journal of American Society for Mass Spectrometry, 2010, 21, 178-190.*
Zhang, et al., Analysis of Pharmaceutical Heparins and Potential Contaminants Using H-NMR and Page, Journal of Pharmaceutical Sciences, Nov. 2009, pp. 4017-4026, vol. 98, No. 11.
Beyer, et al., Quality assessment of unfractionated heparin using H nuclear magnetic resonance spectroscopy, Journal of Pharmaceutical and Biomedical Analysis, 2008, pp. 13-19, vol. 48.
Blossom, et al., Outbreak of Adverse Reactions Associated with Contaminated Heparin, the New England Journal of Medicine, Dec. 18, 2008, pp. 2674-2684, vol. 359.
Guerrini, et al., Orthogonal analytical approaches to detect potential contaminants in heparin, PNAS, Oct. 6, 2009, pp. 16956-16961, vol. 106, No. 40.
Guerrini, et al., Oversulfated chondroitin sulfate is a contaminant in heparin associated with adverse clinical events, Nature Biotechnology, Jun. 2008, pp. 669-675, vol. 26, No. 6.
International Preliminary Report on Patentability from International application no. PCT/JP2011/070851, report issued Apr. 9, 2013.
Jia, H., Regulators scramble to tighten loopholes after heparin debacle, Nature Biotechnology, May 2008, pp. 477-478, vol. 26, No. 5.
Kishimoto, et al., Contaminated Heparin Associated with Adverse Clinical Events and Activation of the Contact System, the New England Journal of Medicine, Jun. 5, 2008, pp. 2457-2467, vol. 358.
Noritaka, English translation, Studies on the Heparin Purity Test (Part 1), Pharm. Regul. Sci., 2008, pp. 651-659, vol. 39(10).
Roden, et al., the Acid Mucopolysaccharides of Furth's Mastocytoma in the Mouse, Acta. Chem. Scand., 1959, p. 2121, vol. 13, No. 10.
Schiller, et al., a Method for the Separation of Acid Mucopolysaccharides: Its Application to the Isolation of Heparin from the Skin of Rats, the Journal of Biological Chemistry, Apr. 1961, pp. 983-987, vol. 236, no. 4.
Schmidt, et al., the determination of small quantities of isomeric chondroitin sulfates, Biochimica Et Biophysica Acta, 1964, pp. 137-140, vol. 83.
Lee et al., "NMR of heparin API; investigation of unidentified signals in the Usp-specified range of 2.12-3.00 ppm", Anal Bioanal Chem 399:651-662 (2011).
Volpi, Nicola, "Purification of heparin, dermatan sulfate and chondroitin sulfate from mixtures by sequential precipitation with various organic solvents" Journal of Chromatography B; Biomedical Applications, 685:27-34(Oct. 11, 1996).

* cited by examiner

*Primary Examiner* — Christine T Mui
(74) *Attorney, Agent, or Firm* — Browdy and Neimark, PLLC

(57) ABSTRACT

The present invention provides a high purity heparin useful to be a pharmaceutical product, cosmetics, research reagent, or the like, and a method for producing the same, more specifically, a heparin which does not substantially contain a nitrous acid degradation-resistant impurity and a method for producing a heparin, comprising mixing an aqueous solution of 5 to 30% by weight of the heparin with ethanol having an amount (volume) 0.2 to 1 times the amount (volume) of the aqueous heparin solution to obtain a colloidal precipitate of heparin.

2 Claims, 7 Drawing Sheets ically synthesis methods, the structure analysis, investigation to determine the causes of adverse events by animal tests, or the like, particularly studying on the purity and safety assessment by $^1$H-NMR, other test methods, or the like, (Non Patent Literatures 5 and 6), and OSCS has been specified as the causative substance of adverse events in Japan and thus safety/purity tests have been reviewed by administration agencies and preparation manufacturers (Non Patent Literatures 7 and 8).

HIGH PURITY HEPARIN AND PRODUCTION METHOD THEREFOR

TECHNICAL FIELD

This patent application claims the priority based on the Japanese Patent Application No. 2010-205310, and the entire disclosure of which is incorporated herein by reference.

The present invention relates to a high purity heparin which does not substantially contain substances causing side effects, is very safe and useful to be a pharmaceutical product, cosmetics, research reagent, or the like, and a method for producing the same.

BACKGROUND ART

Heparin is an acid mucopolysaccharide found in the liver, intestines, lungs, skin, and the like, and contains sulfated D-glucosamine, D-glucuronic acid, L-iduronic acid, and the like.

Heparin has a strong anticoagulant activity, and is hence used to treat disseminated intravascular coagulation syndrome (DIC), treat and prevent various thromboembolisms (venous thrombosis, myocardial infarction, pulmonary embolism, cerebral embolism, thromboembolism in upper and lower extremities, pre/post operation thromboembolism, or the like), prevent the blood coagulation at the occasions of extracorporeal circulation apparatus use for haemodialysis, artificial heart and lung, or the like, vessel catheter insertion, blood transfusion, blood tests, or the like.

Further, heparin is known to have many physiological activities, in addition to the anticoagulant activity, such as lipoprotein lipase activation action, antiplatelet aggregation action, hypotensive action, anticomplementary action, cancer metastasis inhibitory action, inhibitory effect on degranulation from mast cells, local inflammation suppression, analgesic action and blood circulation improving action on muscle tissues, and the like.

Heparin is produced by the extraction/fractionation from tissues of principally healthy edible animals, but, ever since the BSE (bovine spongiform encephalopathy) incidence, heparin used as pharmaceutical products is mostly originated from porcine intestinal mucosa. Typically, the porcine intestinal mucosa is suspended in an aqueous solvent for proteolytic digestion, and subsequently an adsorbent, or the like, (Non Patent Literature 1), is added thereto to extract heparin and other mucopolysaccharides (principally chondroitin sulfate family, heparan sulfate, and the like) as a complex to use as a crude material. Then, the crude material is batch mixed/fractionated to obtain heparin (so-called "unfractionated heparin").

The heparin (unfractionated heparin) obtained by the above method contains mucopolysaccharides (mainly heparan sulfate, chondroitin sulfates B and C) other than the heparin, and it is known that the content thereof varies depending on the crude material and production method. However, the side effects caused by those impurities are roughly confirmed and accepted, and as a result, the unfractionated heparin has been used as a pharmaceutical product for many years.

However, in the early 2008, there were many cases reported in the U.S. and Germany that patients administered with an unfractionated heparin preparation by bolus injection (rapid intravenous injection) experienced unusual side effects, and the incidence eventually caused more than 80 deaths. The US FDA analyzed the unfractionated heparin preparation and the bulk drug thereof and confirmed that they were evidently different from the conventional products, and further revealed that oversulfated chondroitin sulfate (OSCS) was identified to have been present in them (Non Patent Literatures 2 to 4). This does not exist as such in nature, and is believed to have been most likely mixed in at the time of bulk drug production.

Serious side effects were not reported in Japan, but a part of the unfractionated heparin preparations and low molecular weight heparin (LMWH) preparations were recalled which caused serious problems in the stable supply to the market.

Many researchers have been studying on OSCS for scientific synthesis methods, the structure analysis, investigation to determine the causes of adverse events by animal tests, or the like, particularly studying on the purity and safety assessment by $^1$H-NMR, other test methods, or the like, (Non Patent Literatures 5 and 6), and OSCS has been specified as the causative substance of adverse events in Japan and thus safety/purity tests have been reviewed by administration agencies and preparation manufacturers (Non Patent Literatures 7 and 8).

Meanwhile, the methods described in 1) Non Patent Literature 1, 2) Non Patent Literature 9, 3) Non Patent Literature 10, 4) Patent Literature 1, and the like, are known for producing or purifying heparin.

However, there has been no method known for easily and effectively removing impurities such as OSCS, chondroitin sulfate, and the like, from heparin. Further, there has been no method known for easily detecting or measuring such impurities in heparin.

CITATION LIST

Non Patent Literature

Non Patent Literature 1
Roden, L., Dorfman, A., Acta Chemi. Scand. 13, 2121 (1959)
Non Patent Literature 2
Nature Biotechnology, 2008, 26, 669-675
Non Patent Literature 3
The New England Journal of Medicine, 2008, 359, 2674-2684
Non Patent Literature 4
The New England Journal of Medicine, 2008, 358, 2457-2467
Non Patent Literature 5
Beyer, T. et al., Journal of Pharmaceutical and Biomedical Analysis, 48, 13-19 (2008)
Non Patent Literature 6
Guerrini, M. et al., Nature Biotechnology 26, 669-675 (2008)
Non Patent Literature 7
Hashii Noritaka et al., Iyaku Kenkyu ("Pharmaceutical drug research" in Japanese) 39 (10) 651-659 (2008)
Non Patent Literature 8
Jia, H., Nature Biotechnology 26, 477-478 (2008)
Non Patent Literature 9
Schiller, S. et al.: J. Biol. Chem. 236, 983 (1961)
Non Patent Literature 10
Schmidt, M and Dmochowski, A: Biochim. Biophys. Acta 83, 137 (1964)

Patent Literature

Patent Literature 1:
Japanese Patent Laid-Open No. 2002-293804

SUMMARY OF INVENTION

Technical Problem

An object of the present invention is to provide a very safe heparin with high purity without substantially containing impurities such as OSCS, chondroitin sulfate, and the like, a method for producing the same, and a method for confirming the purity of heparin during the process in the production thereof.

Solution to Problem

The present inventors conducted extensive studies to solve the above problem and found that the impurities such as OSCS, chondroitin sulfate, and the like, can be easily and effectively removed when the heparin is fractionated using an organic solvent such as ethanol, or the like, under the predetermined conditions, and further the presence and amounts of these impurities can be confirmed and measured by the HPLC analysis after nitrous acid degradation because these impurities are resistant to the nitrous acid degradation performed under the predetermined conditions, whereby the present invention has been accomplished.

More specifically, the present invention comprises as follows:

[1] A heparin which does not substantially contain a nitrous acid degradation-resistant impurity.
[2] A heparin obtainable by a method comprising mixing an aqueous solution of 5 to 30% by weight of a heparin with an organic solvent having an amount (volume) 0.2 to 1 times the amount (volume) of the aqueous heparin solution to obtain a colloidal precipitate of heparin, wherein the organic solvent is selected from ethanol, methanol, isopropanol, acetone and a mixed solvent thereof.
[3] The heparin according to [2], wherein a salt is dissolved in a concentration of 50 to 500 mM in the aqueous heparin solution.
[4] The heparin according to [3], wherein the salt is selected from sodium chloride and sodium acetate.
[5] The heparin according to any one of [1] to [4], which is colloidal.
[6] The heparin according to any one of [1] to [5], wherein the heparin has a molecular weight in a range of 3000 to 30000 dalton.
[7] A method for producing a heparin, which comprises mixing an aqueous solution of 5 to 30% by weight of a heparin with an organic solvent having an amount (volume) 0.2 to 1 times the amount (volume) of the aqueous heparin solution to obtain a colloidal precipitate of heparin, wherein the organic solvent is selected from ethanol, methanol, isopropanol, acetone and a mixed solvent thereof.
[8] A heparin obtainable by a method comprising mixing an aqueous solution of 5 to 30% by weight of a heparin with an organic solvent having an amount (volume) 0.2 to 1 times the amount (volume) of the aqueous heparin solution to obtain a supernatant fluid containing heparin, wherein the organic solvent is selected from ethanol, methanol, isopropanol, acetone and a mixed solvent thereof.
[9] The heparin according to [8], wherein a salt is dissolved in a concentration of 50 to 500 mM in the aqueous heparin solution.
[10] The heparin according to [9], wherein the salt is selected from sodium chloride and sodium acetate.
[11] The heparin according to any one of [8] to [10], wherein the heparin has a molecular weight in a range of 1500 to 12000 dalton.
[12] A method for producing a heparin, which comprises mixing an aqueous solution of 5 to 30% by weight of a heparin with an organic solvent having an amount (volume) 0.2 to 1 times the amount (volume) of the aqueous heparin solution to obtain a supernatant fluid containing heparin, wherein the organic solvent is selected from ethanol, methanol, isopropanol, acetone and a mixed solvent thereof.
[13] A medicament comprising the heparin according to any one of [1] to [6] and [8] to [11].
[14] The heparin according to any one of [1] to [6] and [8] to [11] for use as a medicament.
[15] A pharmaceutical composition comprising the heparin according to any one of [1] to [6] and [8] to [11].
[16] A method for detecting or measuring a nitrous acid degradation-resistant mucopolysaccharide or a nitrous acid degradable mucopolysaccharide contained in a mucopolysaccharide, which comprises degrading the mucopolysaccharide with nitrous acid.

Advantageous Effect of Invention

The high purity heparin of the present invention does not contain OSCS, and the like, which are substances causing side effects, and is thus very safe and can be very preferably used as a pharmaceutical product, cosmetics, research reagent, or the like.

According to the method for producing a heparin of the present invention, a high purity heparin which does not substantially contain nitrous acid degradation-resistant impurities can be obtained easily. The method is also industrially applicable.

According to the method for detecting or measuring mucopolysaccharides of the present invention, the presence of contamination of other mucopolysaccharides having different properties to the nitrous acid degradation in mucopolysaccharide products can be easily identified and the safety, and the like, of the products can be assured. Further, in the process of producing an intended mucopolysaccharide, the contamination of other mucopolysaccharides having different properties to the nitrous acid degradation can also be easily identified, and the production process of the intended mucopolysaccharide is effectively manageable and the contamination of other mucopolysaccharides into intermediate materials and the final product is thus evitable.

DESCRIPTION OF EMBODIMENTS

Figure 1:
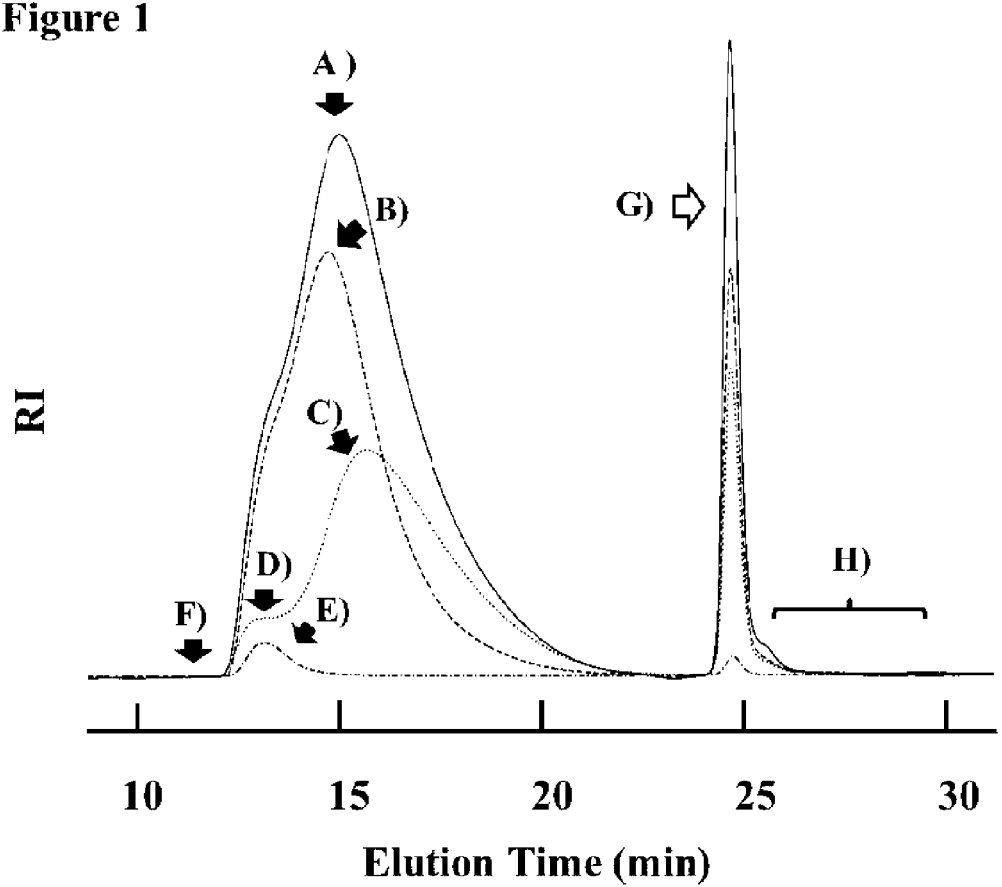
FIG. 1 is an HPLC chart showing the distribution of substances contained in the upper layer (supernatant fluid) and the lower layer (colloidal precipitate) before and after ethanol fractionation of the unfractionated heparin (Na salt, UFN-SP) containing other mucopolysaccharides (mainly heparan sulfate (HS)/chondroitin sulfate B (CSB)). Each letter shown in FIG. 1 means as follows: A) before the ethanol fractionation (solid line), B) the lower layer (colloidal precipitate) after the ethanol fractionation (dashed line), C) the upper layer (supernatant fluid) after the ethanol fractionation (dotted line), D) high molecule mucopolysaccharides with low sulfuration degrees in C) (mainly HS/CSB/CSC) (dotted line), E) mucopolysaccharides resistant to the nitrous acid degradation (mainly CSB/CSC/oversulfated chondroitin sulfate (OSCS)) (dash-dotted line), F) mainly peptidoglycan (dash-dotted line), G) the salt eluted (Na salt) in the mucopolysaccharides (each line), and H) other low molecular weight compounds (ethanol and other unidentified substances) (mainly solid line).

The high purity heparin of the present invention does not substantially contain nitrous acid degradation-resistant impurities.

The "heparin" of the present invention is not particularly limited and may be those obtained from conventionally known raw materials and by conventionally known production methods, and examples include so-called "unfractionated heparin", "low molecular weight heparin" and "heparan sulfate" having a particularly high molecular weight or a particularly high sulfuric acid content among "heparan sulfates" having a structural sugar composition and a coupling scheme analogous to the "heparin", and the like.

The above "unfractionated heparin" means the heparin which is not de-polymerized and typically has a molecular weight in a range of 3000 to 30000 dalton.

The above "low molecular heparin" means the heparin which is de-polymerized to have a low molecule and typically has a molecular weight in a range of 1500 to 12000 dalton.

The above "heparan sulfate" typically has a molecular weight in a range of 3000 to 30000 dalton.

The heparin of the present invention encompasses those generally having the physiological activities or pharmacological activities substantially analogous to the free form in vivo, for example, heparin derivatives and pharmaceutically acceptable salts, addition salts, hydrates, and the like, are included in the technical scope of the present invention.

Additionally, the molecular weight used herein is the weight average molecular weight determined by the HPLC method of size exclusion gel chromatography with an aqueous solvent.

The "nitrous acid degradation" used in the present invention may be the nitrous acid degradation treatment with the conditions under which heparin is substantially degraded and the impurities such as OSCS, chondroitin sulfates, and the like, to be described later, are not degraded, and includes, for example, a nitrous acid degradation treatment carried out under the conditions of a comparatively low pH, low temperature and short time such as pH of 1.0 to 7.0 (preferably pH of 2.0 to 5.0), a reaction temperature of −10 to 40° C. (preferably −5 to 10° C.), a reaction time of 0.5 to 60 minutes (preferably 5 to 15 minutes), an amount of 10 to 1000 mg (preferably 50 to 100 mg) of nitrous acid (particularly sodium nitrite) used to 1 g of reference substance (heparin, etc.), and the like.

The above "nitrous acid degradation-resistant impurity" means the impurities in heparin, which are resistant to the above nitrous acid degradation, and, for example, when analyzed by HPLC (e.g., under the conditions to be described later) after heparin is degraded with nitrous acid, a substance eluted at the point corresponding to the elution point of the heparin before the nitrous acid degradation. Examples of such a substance include mucopolysaccharides having a disaccharide unit structure of galactosamine and uronic acid (glucuronic acid or iduronic acid) as the basic structure, such as oversulfated chondroitin sulfate (OSCS), chondroitin sulfate A (chondroitin-4-sulfate: CSA), B (dermatan sulfate: CSB), C (chondroitin-6-sulfate: CSC), D (chondroitin-2,6-sulfate: CSD), E (chondroitin-4,6-sulfate: CSE), and the like, and keratan sulfate (KC) having a disaccharide unit structure of galactosamine and uronic acid as the basic structure.

The above "does not substantially contain" "a nitrous acid degradation-resistant impurity" means as follows; with respect to the peak total area value detected with the refractive index (RI) appeared at the elution point (e.g., 10 to 20 minutes of an elution time in the specific example below) of the heparin obtained when a reference heparin is analyzed by high performance liquid chromatography (HPLC) under the conditions with reference to the "Molecular Weight" section in the "Parnaparin sodium" Standard Test Method described in The Japanese Pharmacopoeia, fifteenth edition, the peak total area value appeared at the elution point of the heparin when degraded with the above nitrous acid and analyzed by HPLC under the same conditions is 5% or less, preferably 1% or less, more preferably 0.5% or less.

Specific examples of the above HPLC condition include the following conditions:
Detection system: SHIMADZU management system (LC solution), Differential refractometer (RI: RID-10A)
Column and guard column: Tosoh Bioscience TSK gel G-2000SWXL and TSK guard column SWXL
Column temperature: 40° C.
Mobile phase: 0.2 mol/L sodium sulfate (pH 5.0)
Flow rate: 0.5 mL/min.

The high purity heparin of the present invention can be produced by, for example, a method which comprises fractionating a raw material heparin containing nitrous acid degradation-resistant impurities, and the like, using an organic solvent such as ethanol under predetermined conditions.

Examples of the organic solvent used for the above fractionation include ethanol, methanol, isopropanol, acetone or a mixture thereof. Of these, ethanol is the most preferable in consideration of the residue in the final product.

Hereinbelow, the present invention will be described taking, as an example, a procedure using ethanol as the organic solvent (ethanol fractionation), but the present invention can be also carried out using other organic solvents in place of ethanol.

The ethanol fractionation in the present invention comprises mixing a 5 to 30% by weight (preferably 10 to 20% by weight) aqueous heparin solution with ethanol having an amount (volume) 0.2 to 1 times (preferably 0.4 to 0.6 times) the amount (volume) of the aqueous heparin solution to obtain a colloidal precipitate of heparin. This method is simple and industrially applicable.

Conventionally, the ethanol precipitation method has been used to obtain heparin as a white precipitate. However, the concentration of heparin in an aqueous heparin solution according to the conventional ethanol precipitation method is 1 to 5% by weight, which is remarkably lower than the concentration of heparin according to the ethanol fractionation in the present invention. The amount of ethanol with which the aqueous heparin solution is mixed is 2 to 10 times the amount (volume) of the aqueous heparin solution, and is notably larger than the amount of ethanol according to the ethanol fractionation in the present invention. More specifically, the ethanol fractionation in the present invention is clearly distinguished from the conventional ethanol precipitation method.

The raw material heparin in the above ethanol fractionation is not particularly limited, and heparins at various purification stages and impurity concentrations such as raw materials of unfractionated heparin, unfractionated heparin, low molecular weight heparin, or the like, can be used. However, when a desired heparin is recovered in the form of colloidal precipitate, the molecular weight of raw material heparin is preferably 3000 to 30000 dalton, more preferably 5000 to 15000 dalton.

In the above ethanol fractionation, the raw material heparin is dissolved in water such as purified water, water for injection, or the like, so as to give the above concentration range, whereby an aqueous heparin solution is prepared.

The above aqueous heparin solution has preferably a pH value near the acidic to neutral range, and, for example, pH 2.5 to 7.5, preferably pH 4.0 to 7.0, in view of the more rapid precipitation formation by the solvent as the pH of aqueous solution increases, whereas the slower precipitation formation by the solvent as the pH decreases due to the properties of heparin.

The above aqueous heparin solution preferably has a salt dissolved therein because the precipitation formation caused by the solvent becomes more rapid as the ionic strength increases whereas the precipitation formation caused by the solvent becomes slower as the ionic strength decreases due to the properties of heparin, and further a low salt concentration makes it difficult to form a colloidal precipitation and requires a centrifugal operation, or the like. Examples of the salt concentration include 50 to 500 mM, preferably 100 to 250 mM. Examples of the salt include, since heparin is used principally as a pharmaceutical product, pharmaceutically acceptable salts such as sodium chloride, sodium acetate, and the like.

Accordingly, the aqueous heparin solution may be a solution in which heparin is dissolved in physiological saline.

The processing temperature and processing time in the above ethanol fractionation are not particularly limited insofar as a processing temperature and a processing time are those at which a colloidal precipitate of heparin is obtained, and, the ethanol fractionation can be carried out, for example, at a temperature of −10 to 40° C. (preferably 5 to 25° C.) for, for example, 0.5 to 48 hours (preferably 4 to 24 hours).

Owing to the above ethanol fractionation, the nitrous acid degradation-resistant impurities are left in the supernatant fluid but heparin forms a colloidal and precipitates. Consequently, when the colloidal precipitate is separated from the supernatant fluid, a high purity heparin which substantially does not contain the nitrous acid degradation-resistant impurities can be obtained.

The "colloidal" heparin or "colloidal" precipitate in the present invention is the heparin forming a colloidal dispersed phase and which precipitates while forming an interface and a layer in the mixed solution of water and an organic solvent used in the fractionation of the present invention, and means, for example, those in the state which is difficult to be substantially collected by filtration using a microorder molecular size sieve to filter papers such as ultrafiltration membranes (e.g., a molecular weight cutoff of 500 to 50000 MW) commonly used (difficult to separate the precipitate from water/organic solvent mixed solution using a filter paper).

On the other hand, when heparin having a molecular weight of 1500 to 12000, preferably an average molecular weight of 2500 to 7500 is used as the raw material heparin, the above fraction using an organic solvent such as ethanol is preferably carried out as follows.

Examples of the organic solvent used for the fractionation include ethanol, methanol, isopropanol, acetone or a mixture thereof. Of these, ethanol is the most preferable in consideration of the residue in the final product.

Hereinbelow, the above fractionation will be described taking, as an example, a procedure using ethanol as the organic solvent (ethanol fractionation), but the fractionation can be also carried out using other organic solvents in place of ethanol.

The above raw material heparin is dissolved in water such as purified water, water for injection, or the like, so as to give the above concentration range, whereby an aqueous heparin solution is prepared. The pH of the aqueous solution is preferably near the acidic to neutral range, and, for example, pH 2.5 to 7.5, preferably pH 4.0 to 7.0, in view of the more rapid precipitation formation by the solvent as the pH of aqueous solution increases, whereas the slower precipitation formation by the solvent as the pH decreases.

The above aqueous heparin solution preferably has a salt dissolved therein because the precipitation formation caused by the solvent becomes more rapid as the ionic strength increases whereas the precipitation formation caused by the solvent becomes slower as the ionic strength decreases, and further a low salt concentration makes it difficult to form a colloidal precipitation and requires a centrifugal operation, or the like, hence not suitable for batch operation. Examples of the salt concentration include 50 to 500 mM, preferably 100 to 250 mM. Examples of the salt include pharmaceutically acceptable salts such as sodium chloride, sodium acetate, and the like.

The ethanol fractionation comprises mixing an aqueous solution of 5 to 30% by weight (preferably 10 to 20% by weight) of the heparin with ethanol having an amount (volume) 0.2 to 1 times (preferably 0.25 to 0.6 times) the amount (volume) of the aqueous heparin solution to obtain a precipitate of nitrous acid degradation-resistant impurities.

In this case, the nitrous acid degradation-resistant impurities precipitates but heparin is left in the supernatant fluid. Consequently, when the precipitate is separated from the supernatant fluid, a high purity heparin which substantially does not contain the nitrous acid degradation-resistant impurities can be obtained.

After the ethanol fractionation, purification treatment (ethanol precipitation method, etc.), dry treatment (reduced pressure drying, etc.), or the like are carried out in accordance with a routine procedure, thereby obtaining a high purity heparin in the form of a white powder, which does not substantially contain the nitrous acid degradation-resistant impurities.

The high purity heparin obtained in accordance with the present invention substantially does not contain impurities such as OSCS, and the like, which are causative substances of side effects, and is thus very safe and very preferably applicable to pharmaceutical uses, to which the conventional heparins have been applied because of the similar physiological activities to the conventional heparins. For example, the high purity heparin of the present invention has a strong anticoagulant activity, and hence can be used to treat disseminated intravascular coagulation syndrome (DIC), treat and prevent various thromboembolism (venous thrombosis, myocardial infarction, pulmonary embolism, cerebral embolism, thromboembolism in upper and lower extremities, pre/post operation thromboembolism, or the like), prevent the blood coagulation at the occasions of extracorporeal circulation apparatus use for haemodialysis, artificial heart and lung, or the like, vessel catheter insertion, blood transfusion, blood tests, or the like. Further, the high purity heparin of the present invention has many physiological activities such as lipoprotein lipase activation action, antiplatelet aggregation action, hypotensive action, anticomplementary action, cancer metastasis inhibitory action, inhibitory effect on degranulation from mast cells, local inflammation suppression, analgesic action and blood circulation improving action, and the like, and thus can be used as a preventive or therapeutic agent for various diseases based on these activities.

The high purity heparin of the present invention, as in the conventional heparins, can be formulated by the routine method and administered in the form of injection solution or oral agent. For example, the heparin is administered by the following administration method, but the dose and administration rate thereof are determined in accordance with age, conditions, application range or purposes while the whole blood clotting time or whole blood activated partial thromboplastin time is measured usually after the present agent is administered.

For example, for the intravenous infusion method, heparin in an amount equivalent to 5,000 to 50,000 heparin unit is diluted with a 5% glucose injection, physiological saline or 1,000 ml of Ringer's solution and intravenously administered at a rate of about 20 to 30 drips a minute. Moreover, for the intravenous intermittent injection, heparin in an amount equivalent to 5,000 to 50,000 heparin unit is intravenously injected every 4 to 8 hours. For the subcutaneous injection and intramuscular injection, heparin in an amount equivalent to 5,000 to 10,000 heparin unit per injection is subcutaneously or intramuscularly injected every 4 hours.

For use at the time of extracorporeal circulation (haemodialysis, artificial heart and lung), the proper dosage for each patient with an artificial kidney is calculated based on the result of heparin sensitivity test conducted before the dialysis; however, in the case of systemic heparinization, heparin in an amount equivalent to 1,000 to 3,000 heparin unit is typically administered before the dialysis starts and once the dialysis has started, an amount equivalent to 500 to 1,500 heparin unit per hour is continuously, or an amount equivalent to 500 to 1,500 heparin unit per hour is intermittently, added. In the case of regional heparinization, an amount equivalent to 1,500 to 2,500 heparin unit per hour is continuously injected. Further, at the time of artificial heart and lung perfusion, an amount equivalent to 150 to 300 heparin unit/kg is administered, which may vary depending on the surgical form and method, and is additionally administered as necessary in accordance with the time extended for the extracorporeal circulation.

When orally administered, heparin in an amount equivalent to 500 to 2,000 heparin unit/g is taken one to several times a day. In the case of an external preparation, an amount equivalent to 100 to 500 heparin unit/g is used as a heparin ointment, and a proper dose is rubbed or applied as spread over a piece of gauze one to several times a day.

When used as a suppository, heparin in an amount equivalent to 1,000 to 4,000 heparin unit/g is inserted to the anus or vagina once or twice a day.

Moreover, the high purity heparin of the present invention, as in the conventional heparins, can be preferably used as cosmetics, research agents, or the like.

The present invention also provides a method for detecting or measuring nitrous acid degradation-resistant mucopolysaccharides or nitrous acid degradable mucopolysaccharides contained in a mucopolysaccharide, which comprises the degradation of the mucopolysaccharide with nitrous acid.

Examples of the "nitrous acid degradation-resistant mucopolysaccharide" in the above method include the mucopolysaccharides, and the like, described as the examples of the nitrous acid degradation-resistant impurities. Further, the "nitrous acid degradable mucopolysaccharide" means mucopolysaccharides degradable by the above nitrous acid degradation, and examples thereof include heparin, heparan sulfate, and the like.

Furthermore, the "nitrous acid degradation" in the above method is the same as the above nitrous acid degradation.

The mucopolysaccharide used in the above method is not particularly limited, and examples include heparin, heparan sulfate, chondroitin sulfate, keratan sulfate, and the like.

After the nitrous acid degradation of the mucopolysaccharide, for example, nitrous acid degradation-resistant mucopolysaccharides or nitrous acid degradable mucopolysaccharides contained in the mucopolysaccharide can be detected or measured by the HPLC method described above. More specifically, when the reference mucopolysaccharide is analyzed by HPLC after the nitrous acid degradation, in the case where the reference mucopolysaccharide is a nitrous acid degradable mucopolysaccharide (heparin, or the like) and which also contains nitrous acid degradation-resistant mucopolysaccharides (chondroitin sulfate, and the like), the peak corresponding to the nitrous acid degradable mucopolysaccharide before the nitrous acid degradation disappears and the peak corresponding to the nitrous acid degradation-resistant mucopolysaccharides is detected. Conversely, in the case where the reference mucopolysaccharide is a nitrous acid degradation-resistant mucopolysaccharide (chondroitin sulfate, or the like) and which also contains nitrous acid degradable mucopolysaccharides (heparin, and the like), the peak corresponding to the nitrous acid degradation-resistant mucopolysaccharide before the nitrous acid degradation diminishes the intensity corresponding to the nitrous acid degradable mucopolysaccharides after the nitrous acid degradation.

According to the above method for detecting or measuring mucopolysaccharides, the presence of contamination of other mucopolysaccharides having different properties to the nitrous acid degradation in mucopolysaccharide products can be easily identified and the thus safety, and the like, of products can be assured. Further, in the process of producing an intended mucopolysaccharide, the contamination of other mucopolysaccharides having different properties to the nitrous acid degradation can be easily identified, and the production process of the intended mucopolysaccharide is effectively manageable and the contamination of other mucopolysaccharides into intermediate materials and final product is thus evitable.

Hereinafter, the present invention is further described with reference to Examples, but should not be limited thereto.

EXAMPLE

Test Method (1) Nitrous Acid Degradation

The treatment was carried out entirely under ice cooling to reduce the side reaction in the weak acidic region (in the vicinity of pH 4.0) at a high temperature. Also, an amount of sodium nitrite added to each sample was 60 mg per 1 g of the sample to avoid the accumulation of excess sodium nitrite after completion of the reaction.

A predetermined amount of sodium nitrite was added to each sample solution dissolved in an injection solution (a Japanese pharmacopoeia compliant product) in advance, stirred and adjusted a pH value to about 1.5 with HCl to start the reaction. 30 minutes later, the pH value was adjusted to 5.0 with NaOH to terminate the reaction, and ethanol was added to solidify and dry, thereby obtaining a white powder.

(2) HPLC Method

The molecular weight distribution of the substances contained in each sample was confirmed by the HPLC method. The conditions for HPLC method were in conformity with the "Molecular Weight" section in the "Parnaparin sodium" Standard Test Method described in The Japanese Pharmacopoeia, fifteenth edition. The conditions for HPLC employed are shown below.

Detection system: SHIMADZU management system (LC solution), Differential refractometer (RI: RID-10A)
Column and guard column: Tosoh Bioscience TSK gel G-2000SWXL and TSK guard column SWXL
Column temperature: 40° C.
Mobile phase: 0.2 mol/L sodium sulfate (pH 5.0)
Flow rate: 0.5 mL/min.

Reference Example 1

Figure 2:
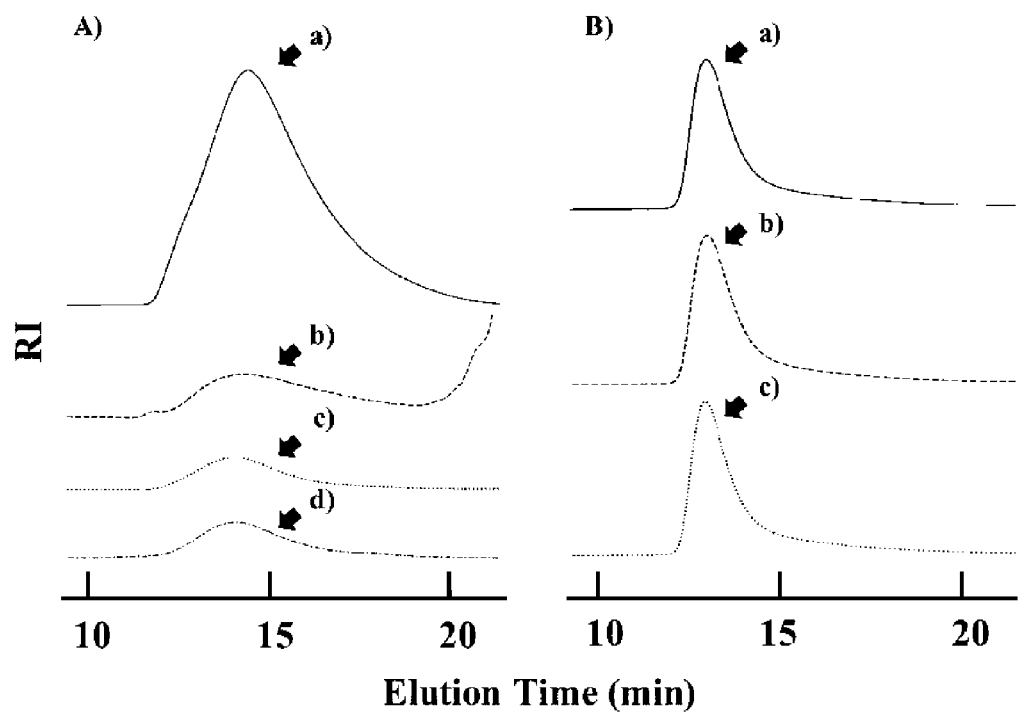
FIG. 2 is an HPLC chart showing changes in the molecular weight before and after the nitrous acid degradation of an OSCS reference substance by the nitrous acid degradation, more specifically, of a crude OSCS (CSMS-CE1 and -CE2), that is, a mixture of OSCS-containing unfractionated heparin (containing about 12.5% of Na salt, OSHP-SH and OSCS), OSCS standard product (OSCS-STD), and OSCS and the chondroitin sulfate family. Each letter shown in FIG. 2 means as follows: A) OSHP-SH and OSCS-STD, a) OSHP-SH before the nitrous acid degradation (solid line), b) OSHP-SH after the nitrous acid degradation (dashed line), c) OSCS-STD before the nitrous acid degradation (dotted line), d) OSCS-STD after the nitrous acid degradation (dashed-dotted line), B) CSMS-CE1 and -CE2, a) CSMS-CE1 after the nitrous acid degradation (solid line), b) CSMS-CE2 after the nitrous acid degradation (dashed line), c) CSB-STD (dotted line).

Each of oversulfated chondroitin sulfate (OSCS) standard product (OSCS-STD, Nippon Koteisho Kyokai), OSCS-containing unfractionated heparin (Na salt, OSHP-SH, an OSCS content of about 12.5%, a product of C company, lot No. 1060-07-0033), and a crude OSCS (CSMS-CE1 and -CE2, prepared by reducing a content of heparin/heparan sulfate to about 95% or less from an N company OSCS-containing unfractionated heparin (Na salt: lot No. PH-64107 and pH-64507)) that is a mixture of OSCS and chondroitin sulfate family was degraded with nitrous acid by the above method, and HPLC was carried out by the method described above to confirm the molecular weight changes before and after the nitrous acid degradation (FIG. 2). As a result, the degradation and low molecularization with the disaccharide unit-induced peak shifts were not found in OSCS-STD or CSMS-CE1 and -CE2. OSHP-SH (OSCS content is about 12.5%) was found to have the degradation and low molecularization with the disaccharide unit-induced peak shift, and the peak area value of the undegraded product by nitrous acid degradation detected by RI was about 12.1% of the peak area value of before the nitrous acid degradation. Further, the peak of undegraded OSHP-SH showed the molecular weight close to the peak of OSCS-STD (FIG. 2-A). Furthermore, the peaks of CSMS-CE1 and -CE2 showed the molecular weights close to chondroitin sulfate B (CSB-STB, purity>95%, prepared using porcine intestinal mucosa extracts) (FIG. 2-B).

Reference Example 2

Figure 3:
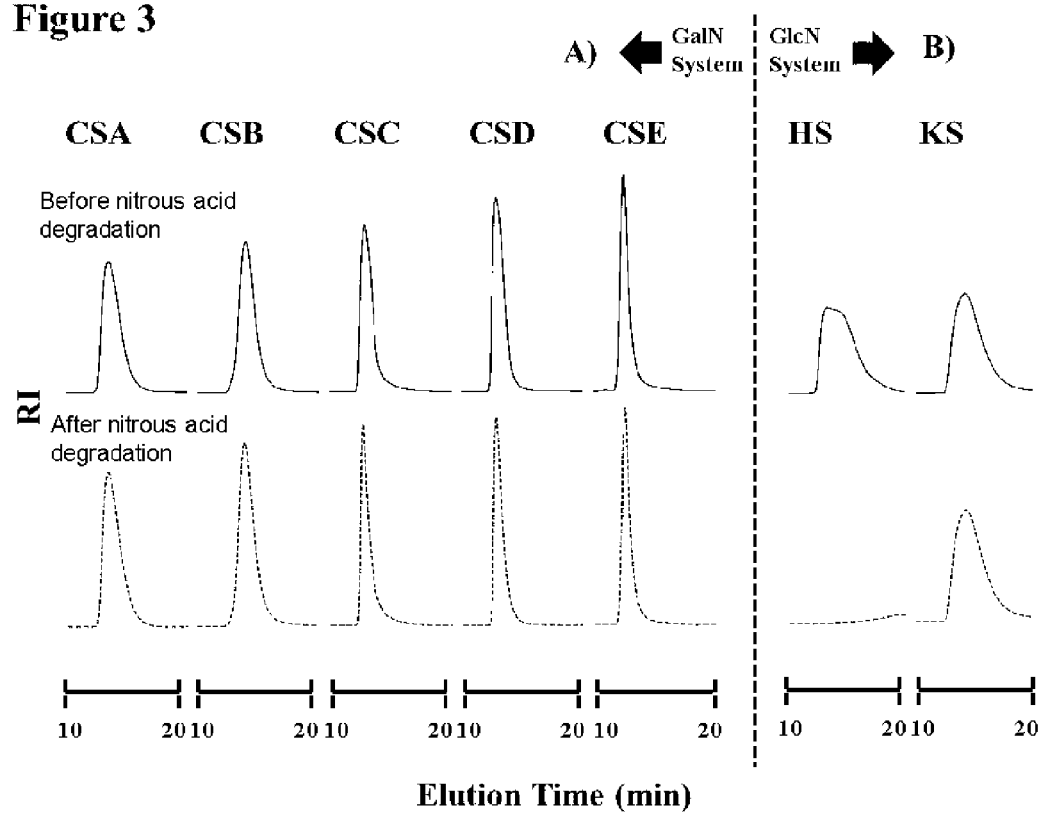
FIG. 3 is an HPLC chart showing changes in the molecular weight of mucopolysaccharide reference substances by the nitrous acid degradation, more specifically, chondroitin sulfate family (CSA, CSB, CSC, CSD and CSE), heparan sulfate (HS) and keratan sulfate (KS). (Before the nitrous acid degradation: solid line, after the nitrous acid degradation: dashed line).

Types A, B, C, D and E (CSA, CSB, CSC, CSD and CSE) of the chondroitin sulfate family (special grade reagents), heparan sulfate (HS) and keratan sulfate (KS) were purchased from SEIKAGAKU CORPORATION, degraded with nitrous acid by the above method and subjected to HPLC by the above method to confirm the molecular weight changes before and after the nitrous acid degradation (FIG. 3, left from the dotted line). As a result, the degradation and low molecularization with the disaccharide unit-induced peak shifts were not found in the chondroitin sulfate family and KS. On the other hand, HS was confirmed to have the degradation and low molecularization with the disaccharide unit-induced peak shift (FIG. 3, right from the dotted line).

The results from Reference Examples 1 and 2 revealed that oversulfated chondroitin sulfate (OSCS) and the chondroitin sulfate family (CSA, CSB, CSC, CSD and CSE) are resistant to the nitrous acid degradation, whereas heparan sulfate (HS) is degradable by the nitrous acid degradation.

Example 1

As a sample, unfractionated heparin (Na salt, UFN-SP, a product of C company, lot No. 1035-0792) containing other mucopolysaccharides (mainly heparan sulfate/chondroitin sulfate B/chondroitin sulfate C) (500 g) was weighed and put into a 10 L enamel tank and physiological saline (the Japanese pharmacopoeia compliant product) was added thereto to give 5 L (pH 6.0). Ethanol (2.5 L; Wako Pure Chemical Industries, Ltd., a special grade reagent) was added to this solution, stirred and allowed to stand at room temperature (25° C.) for 24 hours or more (ethanol fractionation). After confirming that the reaction solution has been divided into two layers of the colloidal precipitate (lower layer) and the supernatant fluid (upper layer), the supernatant fluid was transferred to a 30 L enamel tank, ethanol (20 L) was added thereto and stirred vigorously. The colloidal precipitate was transferred to a 30 L enamel tank, physiological saline (3 L) was added and stirred, and ethanol (20 L) was added thereto and stirred vigorously. After each treatment, the resulting products were allowed to stand for 24 hours. The white deposits precipitated at the bottom of both tanks were collected respectively in a Buchner funnel, washed with ethanol and dried at room temperature for 24 hours under reduced pressure in the presence of phosphorus pentaoxide. 418.2 g of a white powder was finally recovered from the colloidal precipitate (recovery rate 83.6%).

The above UFN-SP was examined by the above HPLC method for the distributions of the substances contained in the upper layer (supernatant fluid) and the lower layer (colloidal precipitate) before and after the ethanol fractionation. The results are shown in FIG. 1.

Further, the obtained products were degraded with nitrous acid in accordance with the above method, and the amounts of substances (heparin and nitrous acid degradation-resistant impurities) contained in the products before and after the nitrous acid degradation were determined as the peak total area appeared between 10 and 20 minutes of the elution time by carrying out HPLC in accordance with the above method. The results are shown in Table 1.

Comparative Example 1

The above UFN-SP was degraded with nitrous acid in accordance with the above method. The distributions of the substances contained in the sample before and after the nitrous acid degradation were confirmed by the HPLC method. Further, the amounts of substances (heparin and nitrous acid degradation-resistant impurities) contained in the products before and after the nitrous acid degradation were determined as the peak total area appeared between 10 and 20 minutes of the elution time by carrying out HPLC in accordance with the above method. The results are shown in Table 1.

Comparative Examples 2 to 7

Figure 4:
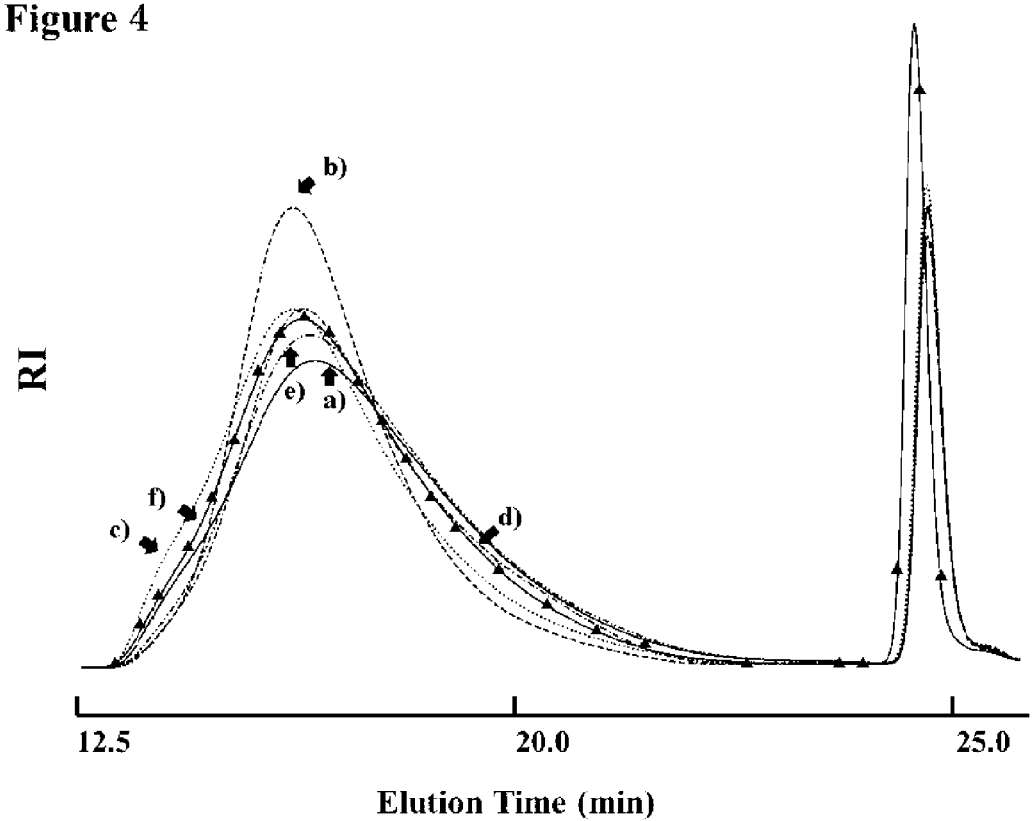
FIG. 4 is an HPLC chart showing the molecular weight distributions before the nitrous acid degradation of Na salt (UFN 1 to 5) and Ca salt (UFC) in each unfractionated heparin before the ethanol fractionation. Each letter shown in FIG. 4 means as follows: a) UFN1 (solid line), b) UFN2 (dashed line), c) UFN3 (dotted line), d) UFN4 (dash-dotted line), e) UFN5 (double-dotted line), f) UFC (▲ solid line).
Figure 5:
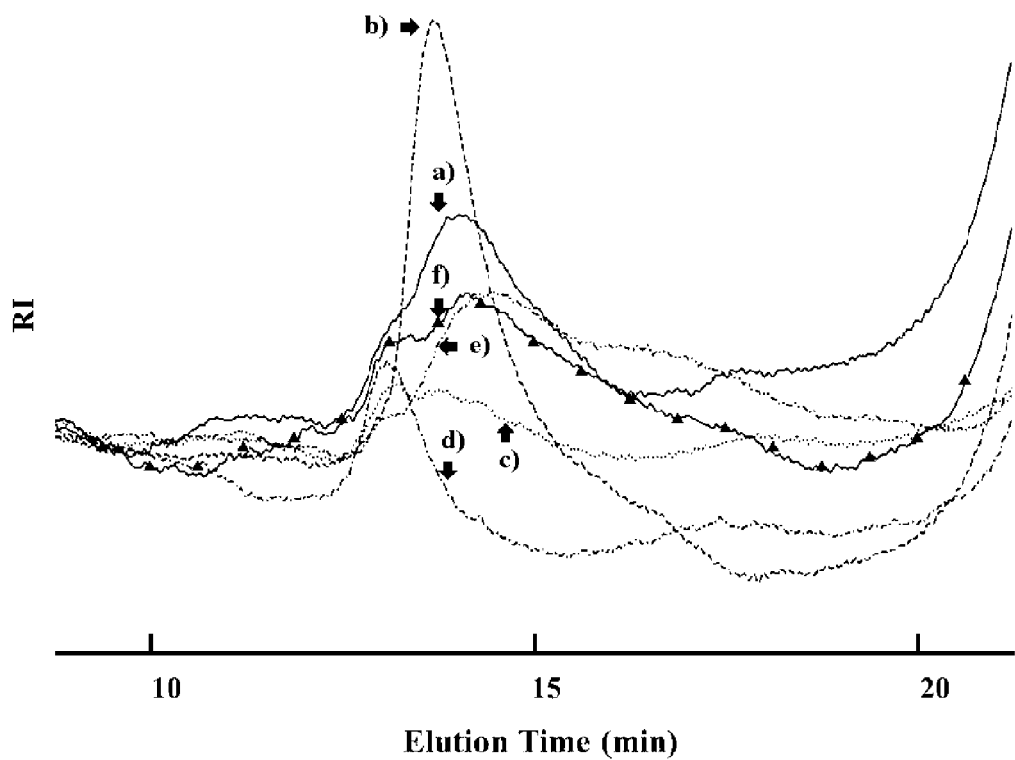
FIG. 5 is an HPLC chart showing the molecular weight distributions after the nitrous acid degradation of Na salt (UFN 1 to 5) and Ca salt (UFC) in each unfractionated heparin before the ethanol fractionation. Each letter shown in FIG. 5 means as follows: a) UFN1 (solid line), b) UFN2 (dashed line), c) UFN3 (dotted line), d) UFN4 (dash-dotted line), e) UFN5 (double-dotted line), f) UFC (▲ solid line).

Five samples of Na salt (UFN 1 to 5) and 1 sample of Ca salt (UFC), wherein it was already confirmed that the OSCS-derived signal was not detected with naked eyes or was not the heparin $^{13}C$ satellite signal in the test using the $^{1}H$-NMR method, were degraded with nitrous acid by the above method. The distributions of the substances contained in the samples before and after the nitrous acid degradation were confirmed by the HPLC method (FIGS. 4 and 5). Further, the amounts of substances (heparin and nitrous acid degradation-resistant impurities) contained in the products before and after the nitrous acid degradation were determined as the peak total area appeared between 10 and 20 minutes of the elution time by carrying out HPLC in accordance with the above method. The results are shown in Table 1.

Examples 2 to 7

Figure 6:
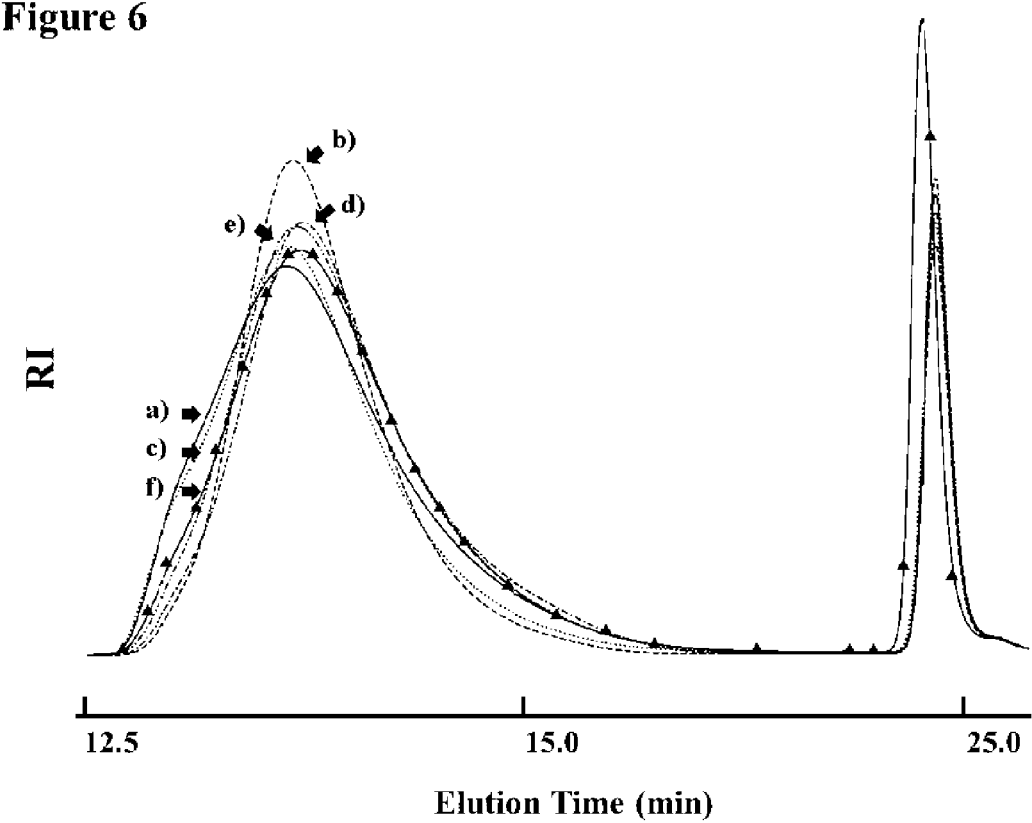
FIG. 6 is an HPLC chart showing the molecular weight distributions before the nitrous acid degradation of Na salt (UFN 1 to 5) and Ca salt (UFC) in each unfractionated heparin after the ethanol fractionation. Each letter shown in FIG. 6 means as follows: a) UFN1 (solid line), b) UFN2 (dashed line), c) UFN3 (dotted line), d) UFN4 (dash-dotted line), e) UFN5 (double-dotted line), f) UFC (▲ solid line).
Figure 7:
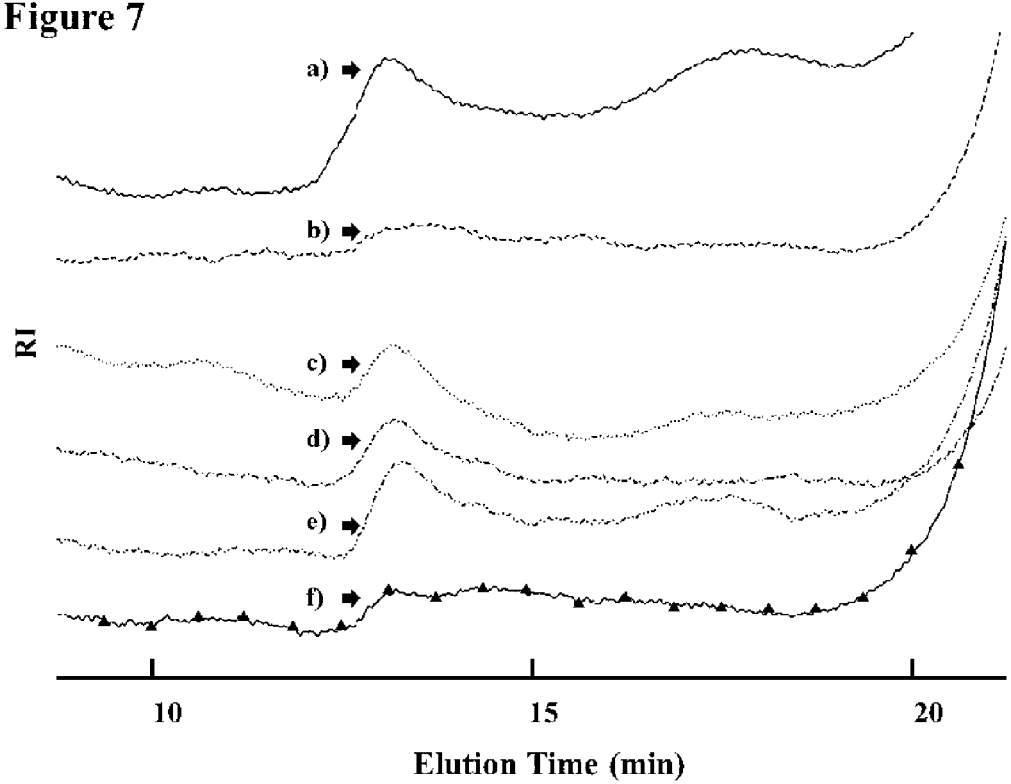
FIG. 7 is an HPLC chart showing the molecular weight distributions after the nitrous acid degradation of Na salt (UFN 1 to 5) and Ca salt (UFC) in each unfractionated heparin after the ethanol fractionation. Each letter shown in FIG. 7 means as follows: a) UFN1 (solid line), b) UFN2 (dashed line), c) UFN3 (dotted line), d) UFN4 (dash-dotted line), e) UFN5 (double-dotted line), f) UFC (▲ solid line).

Samples the same as those of the above Comparative Examples 1 to 6 were subjected to the ethanol fractionation in the same manner as Example 1. Subsequently, each of the obtained products was degraded with nitrous acid in accordance with the above method. The distributions of the substances contained in the samples before and after the nitrous acid degradation were confirmed by the HPLC method (FIGS. 6 and 7). Further, the amounts of the substances (heparin and nitrous acid degradation-resistant impurities) contained in the products before and after the nitrous acid degradation were determined as the peak total area appeared between 10 and 20 minutes of the elution time by carrying out HPLC in accordance with the above method. The results are shown in Table 1.

TABLE 1

| Heparin | Comparative Examples 1-7 Before ethanol fractionation | | | Examples 1-7 After ethanol fractionation | | |
|---|---|---|---|---|---|---|
| | Before nitrous acid degradation (A)[X] | After nitrous acid degradation (B)[X] | (B)/(A) | After nitrous acid degradation (C)[X] | (C)/(B) | (C)/(A) |
| UFN-SP | 2942810 | 34064 | 1.15753% | 2831 | 8.31% | 0.09621% |
| UFN1 | 3139209 | 8714 | 0.27759% | 2723 | 31.25% | 0.08675% |
| UFN2 | 3225737 | 11122 | 0.34479% | 1039 | 9.35% | 0.03222% |
| UFN3 | 3167162 | 303 | 0.00958% | 98 | 32.26% | 0.00309% |
| UFN4 | 3191825 | 607 | 0.01901% | 152 | 25.00% | 0.00475% |
| UFN5 | 3223922 | 2275 | 0.07056% | 479 | 21.05% | 0.01486% |
| UFC | 3218608 | 2528 | 0.07853% | 486 | 19.23% | 0.01510% |

[X]Peak total area appeared between 10 and 20 minutes of elution time

The invention claimed is:

1. A method for detecting or measuring a nitrous acid degradation-resistant mucopolysaccharide or a nitrous acid degradable mucopolysaccharide contained in a mucopolysaccharide, which comprises:
   i) degrading the mucopolysaccharide with nitrous acid at pH of 1.0 to 7.0, a reaction temperature of −10 to 40° C., a reaction time of 0.5 to 60 minutes, and an amount of 10 to 1000 mg of nitrous acid used to 1 g of the mucopolysaccharide; and
   ii) analyzing the degraded product of the step (i) by HPLC.

2. A method for detecting or measuring a nitrous acid degradation-resistant mucopolysaccharide or a nitrous acid degradable mucopolysaccharide contained in a mucopolysaccharide composition, which comprises:

i) treating the mucopolysaccharide composition with nitrous acid at pH of 1.0 to 7.0, a reaction temperature of −10 to 40° C., a reaction time of 0.5 to 60 minutes, and an amount of 10 to 1000 mg of nitrous acid used to 1 g of the mucopolysaccharide, thereby obtaining a modified mucopolysaccharide composition comprising nitrous acid degradation-resistant mucopolysaccharides and/or one nitrous acid degraded mucopolysaccharide, the latter derived by degradation of said nitrous acid degradable mucopolysaccharide; and ii) analyzing the modified mucopolysaccharide composition of the step (i) by HPLC for said nitrous acid degraded mucopolysaccharide and/or said nitrous acid degradation-resistant mucopolysaccharide, thereby detecting or measuring a nitrous acid degradation-resistant mucopolysaccharide or a nitrous acid degradable mucopolysaccharide contained in a mucopolysaccharide composition.

* * * * *